United States Patent [19]

Lenhart

[11] Patent Number: 5,006,718
[45] Date of Patent: Apr. 9, 1991

[54] X-RAY SHIELD FOR X-RAY EXAMINATION TABLE

[76] Inventor: Mark J. Lenhart, 10 Partridge La., Burlington, Mass. 01803

[21] Appl. No.: 383,201

[22] Filed: Jul. 21, 1989

[51] Int. Cl.⁵ .............................................. G21F 3/00
[52] U.S. Cl. ................................ 250/519.1; 250/515.1
[58] Field of Search ............... 250/519.1, 518.1, 517.1, 250/516.1, 515.1; 378/203, 204, 177, 208, 209; 248/298, 285, 286, 279; 160/214, 210, 335, 123, 125; 211/169, 162

[56] References Cited

U.S. PATENT DOCUMENTS

| | | | |
|---|---|---|---|
| 1,907,523 | 5/1933 | Egressi et al. | |
| 2,048,909 | 7/1936 | Woodworth | 160/210 |
| 2,491,756 | 12/1949 | Muench | |
| 2,584,874 | 2/1952 | Haas | 160/214 |
| 2,586,561 | 2/1952 | Poggi | 160/235 |
| 2,689,003 | 9/1954 | Helbert et al. | 160/214 |
| 2,718,598 | 9/1955 | Graf | |
| 2,812,534 | 11/1957 | Graber | |
| 3,151,244 | 9/1964 | Savouyaud et al. | 250/515.1 |
| 3,682,226 | 8/1972 | Ford | 160/330 |
| 3,957,251 | 5/1976 | McCracken | 160/223 |
| 3,967,129 | 6/1976 | Winkler | 250/517.1 |
| 3,984,696 | 10/1976 | Collica et al. | 250/519.1 |
| 4,062,518 | 12/1977 | Stivender et al. | 250/519 |
| 4,083,395 | 4/1978 | Romano | 160/84 R |
| 4,254,341 | 3/1981 | Herr et al. | 250/519.1 |
| 4,276,919 | 7/1981 | Walters | 160/235 |
| 4,385,409 | 5/1983 | File et al. | 4/608 |
| 4,460,833 | 7/1984 | Malamud et al. | 250/519.1 |
| 4,472,637 | 9/1984 | Sportelli et al. | 250/515.1 |
| 4,581,538 | 4/1986 | Lenhart | 250/519.1 |
| 4,583,715 | 4/1986 | Wright | 160/225 |
| 4,638,166 | 1/1987 | Baudro | 250/515.1 |

*Primary Examiner*—Jack I. Berman
*Assistant Examiner*—Kiet T. Nguyen

[57] ABSTRACT

An X-ray shield comprises an elongated mounting bar having a linear main section and linear hinge section hingedly connected together, a mounting bracket on one side of the linear main section adapted for connection to the accessory rod on the side of an X-ray examination table and draped opaque to X-ray extending from the mounting bar to the floor to protect personnel from X-ray radiation emanating from below the examination table.

5 Claims, 3 Drawing Sheets

X-RAY SHIELD FOR X-RAY EXAMINATION TABLE

BACKGROUND OF THE INVENTION

This invention relates to X-ray shielding which prevents X-rays from contacting a person working in close proximity to a source of X-rays.

Malamud et al., U.S. Pat. No. 4,460,833, describe a wheelchair having a radiation shield mounted to it in order to shield an attendant from any radio isotopes present within the patient.

Lenhart, U.S. Pat. No. 4,581,538, describes an X-ray shield formed as a flexible, mechanically penetrable curtain. The curtain is formed of flexible radiation shielding flaps.

Winkler, U.S. Pat. No. 3,967,129, describes a radiation shield formed as a stranded curtain made up of bead chains. These chains offer minimal obstruction to the radiologist.

Baudro, U.S. Pat. No. 4,638,166, describes a portable collapsible radiation shielding device formed from horizontally aligned slats.

Collica et al, U.S. Pat. No. 3,984,696, describes a radiation guard formed of adjacent strips through which a hand may be inserted.

SUMMARY OF THE INVENTION

The invention features an X-ray shield for preventing passage of X-rays in front of the shield to a person positioned behind the shield. The shield is adapted for attachment to an x-ray examination table, e.g., an angiographic table, having a horizontally positioned accessory rod adjacent the upper portion of the table. The table is positioned above a floor and a source of X-rays may cause X-rays to pass between the floor and the table. The shield includes an elongated mounting bar having a linear main section and a linear hinge section. These two sections are connected together at one end by a hinge. The hinge is constructed and arranged to allow horizontal rotational movement of the linear hinge section about the hinge when the linear main section is fixedly held in a horizontal position. Also provided is a mounting bracket fixedly connected to one side of the linear section. The bracket is constructed and arranged to be slidingly engaged with the accessory rod to hold the mounting bar in a horizontal position adjacent the angiographic table. It is also constructed and arranged to allow the horizontal rotational movement of the linear hinge section. The shield also includes a drape formed substantially of an X-ray opaque material fixed at one edge to the mounting bar and extending from the mounting bar substantially the distance the mounting bar is spaced from the floor. The drape is adapted to allow horizontal rotational movement of the linear hinge section. The drape is designed to prevent the passage of X-rays from one side of the drape between the table and the floor and the other side of the drape.

In preferred embodiments the mounting bar includes two elongated hanging bars one fixedly connected to each of the linear main section and the linear hinge section, and adapted to hold the edge of the drape; the drape includes an elongated channel at the edge of the drape, the channel being constructed and arranged to allow the hanging bars to be inserted within the channel and thereby hold the drape to the mounting bar; a locking nut is provided and adapted to fix the shield in a horizontal position on the accessory rod; and the shield further comprises a second mounting bracket spaced from the other mounting bracket along the linear main section.

The X-ray shield of the present invention provides medical personnel with extra protection from scattered X-rays. Angiographic tables generally have a source of X-rays located below the table, and above the floor on which the table is positioned. It is common to protect personnel from this source of X-rays by having them wear heavy lead aprons. The present invention makes it possible for several people to work close to the source of X-rays without individual X-ray protection, since it prevents the emission of X-rays from below the table. It may be used in conjunction with shielding above the table. The shield of the invention is designed for fixed and sliding connection to any standard angiographic table using the existing accessory rod mounted on such tables. The shield may be placed on either or both sides of the table and the hinged section readily moved to insure complete protection of personnel within the room.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

STRUCTURE

Figure 1:
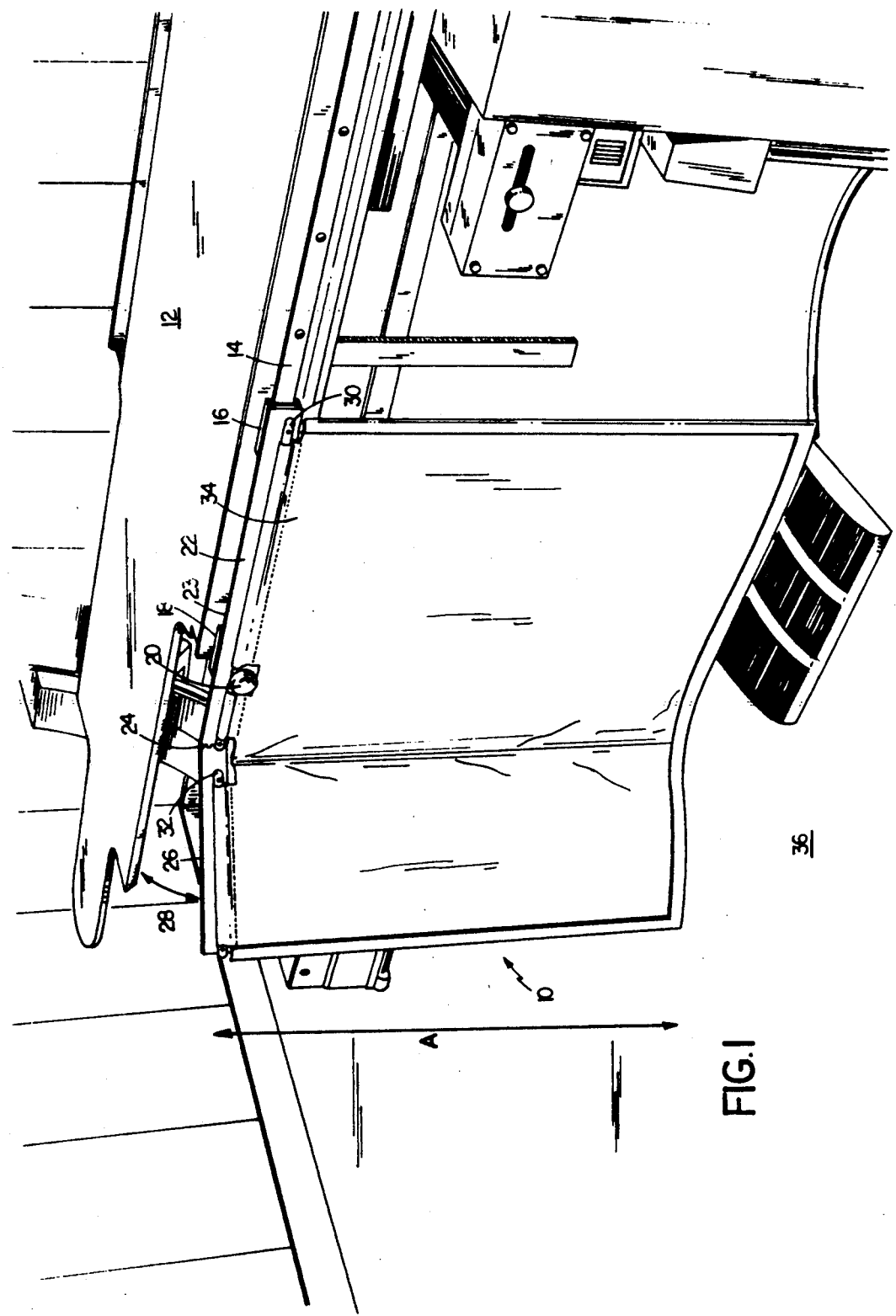
FIG. 1 is an isometric view of an X-ray shield of the invention attached to an angiographic table.

Referring to FIG. 1, X-ray shield 10 is attached to an angiographic table 12 at standard accessory rod 14. The X-ray shield is attached by a pair of brackets 16, 18, and locked horizontally in position by locking nut 20. Brackets 16 and 18 act to hold an elongated mounting bar 22 in a horizontal position adjacent the angiographic table. The elongated mounting bar is formed of two sections, a linear main section 23, and a linear hinge section 26. These sections are held together by a hinge 24 and the linear hinge section is free to move about the hinge, as shown by arrow 28, in a horizontal plane. The hinge provides sufficient friction to insure that the linear hinge section will remain securely in any position in which it is placed. Fixedly attached to the mounting bar is a pair of hanging bars 30 and 32 which are inserted within an X-ray opaque drape 34. The drape extends from the hanging bars at least the distance from the hanging bar to the floor 36 of the operating room. Generally this distance is approximately 3-4 feet.

Figure 2:
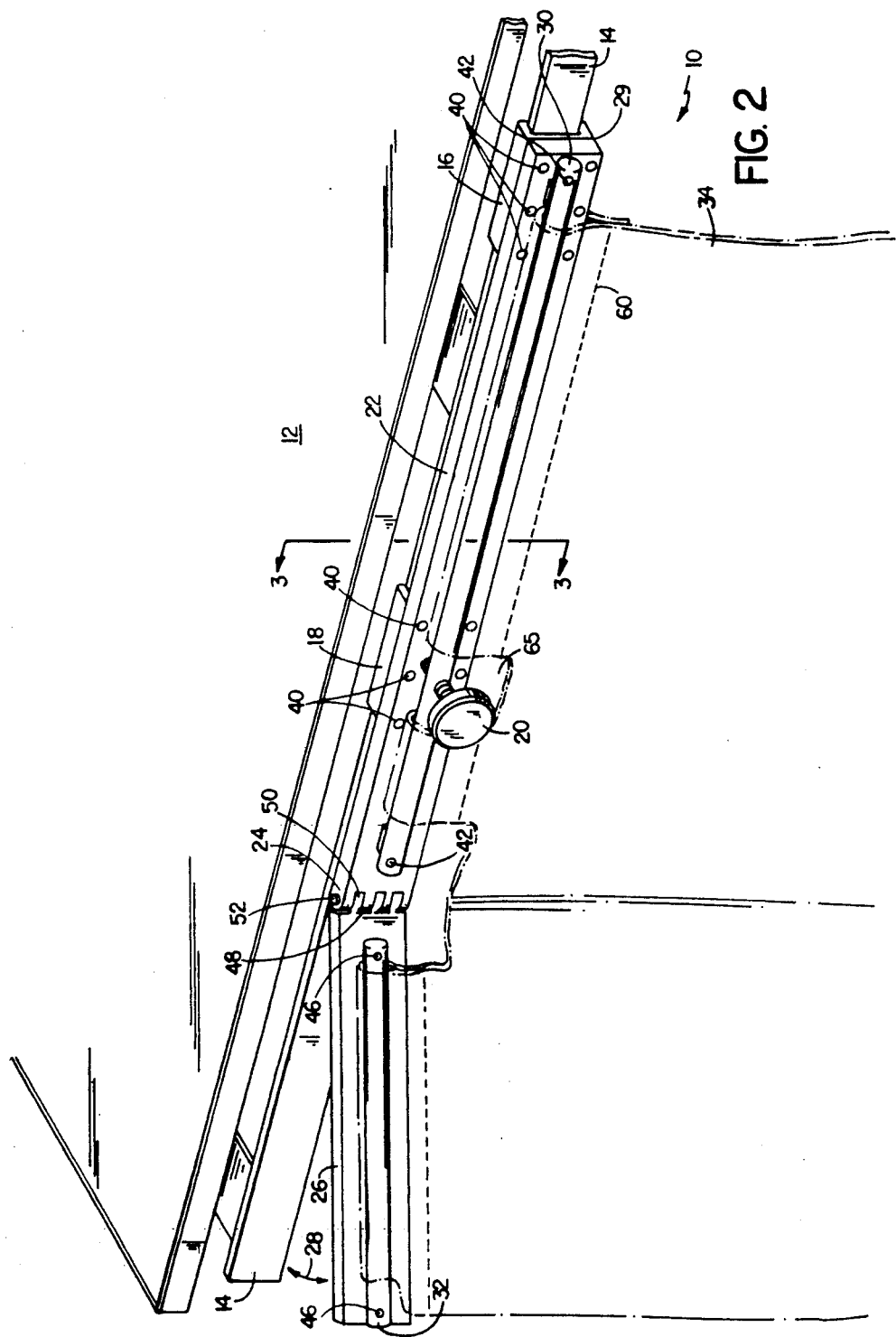
FIG. 2 is an isometric view of the front of a mounting bar and its relationship to an angiographic table.
Figure 3:
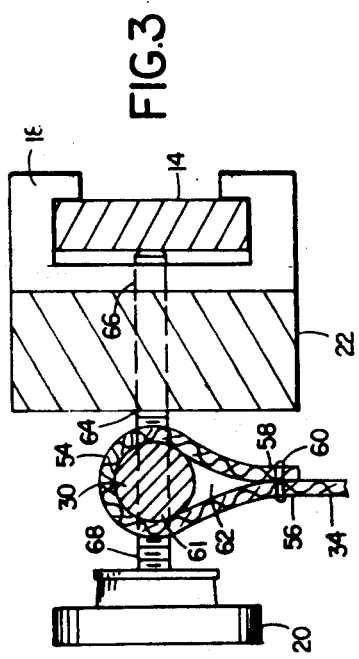
FIG. 3 is a generally sectional view of a locking nut.
Figure 4:
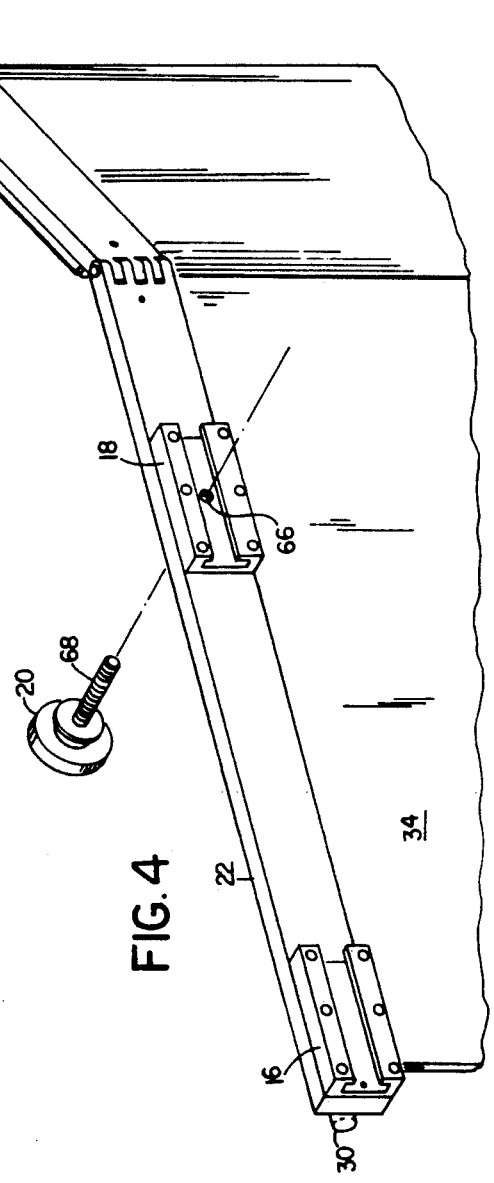
FIG. 4 is an isometric view of the back of a mounting bar.

Referring now to FIGS. 2, 3, and 4, the elongated mounting bar 22 is formed from any standard metal, for example, stainless steel, having a length of approximately 2-3 feet and a generally rectangular cross-section. Brackets 16 and 18 are mounted by screws or rivets 40 and are spaced apart about 2 feet, with bracket 16 being fixed to one edge 29 of the mounting bar.

Hanging bar 30 is fixed to the mounting bar by screws or rivets 42 such that it is horizontally positioned when the mounting bar is mounted to an angiographic table accessory rod. Similarly, hanging bar 32 is mounted by screws or rivets 46 to the linear hinge section. Hinge 24 is a standard hinge having interlocking tongues 48 and grooves 50, and an interlocking pin 52. Drape 34 has a top edge 54 which loops around the hanging bars. The front side 56 of the drape is connected to the rear side 58 by stitching 60 or by any other means, for example, by Velcro. The drape thus forms a channel 62 in which the hanging bars reside.

Referring to FIG. 3, locking nut 20 is inserted through an aperture 61 in hanging bar 30, a threaded aperture 64 in linear section 22, and an aperture 66 in mounting bracket 18. The threaded part 68 of locking nut 20 is sized to mate with threaded aperture 64 and can be caused to pass through each of these apertures and contact accessory rod 14. A cut out 65 is provided in the drape to prevent interference with the locking nut.

USE

The X-ray shield of this invention is mounted to the accessory rod of an angiographic table by sliding both of the mounting brackets horizontally along the accessory rod. When it is suitably positioned the locking nut is threaded through the apertures provided within one of the brackets until it contacts the accessory rod and thereby prevents horizontal movement. The hinged portion of the X-ray shield is caused to move in a horizontal manner about the hinge, and can be positioned to ensure that personnel working in front of the shield are protected from X-ray sources behind the shield.

Other embodiments are within the following claims.

I claim:

1. An X-ray shield for preventing passage of X-rays in front of said shield to a person positioned behind said shield, said shield being adapted for attachment to an X-ray examination table having a horizontally positioned accessory rod adjacent the upper portion of the table, wherein said table is positioned above a floor, and a source of X-rays may cause X-rays to pass between the floor and the table, the shield comprising:

an elongated mounting bar comprising a linear main section and a linear hinge section each fixedly connected together at one end by a hinge, wherein said hinge is constructed and arranged to allow horizontal rotational movement of said linear hinge section above said hinge when said linear main section is fixedly held in a horizontal position.

a mounting bracket fixedly connected to one side of said linear section, said bracket being constructed and arranged to be horizontally slidingly engaged with the accessory rod to hold said mounting bar in a horizontal position adjacent the table, to allow said linear section to be horizontally moved and to allow said horizontal rotational movement of said linear hinge section, and a drape comprising an X-ray opaque material, fixed at one edge to said mounting bar and extending from said mounting bar substantially the distance said mounting bar is spaced from the floor, said drape being adapted to allow said horizontal rotational movement of said linear hinge section; wherein said drape prevents the passage of X-rays from one side of said drape between the table and the floor and the other side of said drape.

2. The shield of claim 1 wherein said mounting bar comprises two elongated hanging bars, one fixedly connected to each of said linear main section and said linear hinge section at the opposite side to said mounting bracket, and adapted to hold said edge of said drape.

3. The shield of claim 2 wherein said drape comprises an elongated channel at said edge of said drape, said channel being constructed and arranged to allow said hanging bars to be inserted within said channel and thereby hold said drape to said mounting bar.

4. The shield of claim 1 further comprising a locking nut adapted to fix said shield in a horizontal position on the accessory rod.

5. The shield of claim 1 comprising a pair of mounting brackets spaced from each other along said linear main section.

* * * * *